United States Patent
Ruhe

(10) Patent No.: US 6,602,906 B1
(45) Date of Patent: Aug. 5, 2003

(54) METHOD FOR DELIVERING ASCORBIC ACID AND ACETONE TO THE DERMAL LAYER OF THE SKIN

(76) Inventor: Rodney Charles Ruhe, 1122 Halifax Ave., Davis, CA (US) 95616

( * ) Notice: Subject to any disclaimer, the term of this patent is extended or adjusted under 35 U.S.C. 154(b) by 0 days.

(21) Appl. No.: 09/683,994

(22) Filed: Mar. 9, 2002

(51) Int. Cl.$^7$ ............................ A61K 31/34; A61K 7/00
(52) U.S. Cl. ..................... 514/474; 514/937; 514/938; 424/401
(58) Field of Search ................................ 514/474, 937, 514/938; 424/401

(56) References Cited

U.S. PATENT DOCUMENTS

| | | | | |
|---|---|---|---|---|
| 5,536,500 A | * | 7/1996 | Galey et al. ................ | 424/401 |
| 5,780,504 A | * | 7/1998 | Ptchelintsev ................ | 424/401 |
| 6,014,910 A | * | 1/2000 | Oda et al. ................... | 74/500.5 |
| 6,194,452 B1 | * | 2/2001 | Murad .......................... | 424/60 |
| 6,217,914 B1 | * | 4/2001 | Meisner ....................... | 424/641 |

FOREIGN PATENT DOCUMENTS

JP          11-255647       *    9/1999

* cited by examiner

*Primary Examiner*—Raymond Henley, III
*Assistant Examiner*—Vickie Kim
(74) *Attorney, Agent, or Firm*—Mark C. Jacobs

(57) ABSTRACT

The present invention provides a more efficient method of delivering therapeutically effective amounts of ascorbic acid and acetone to the dermal layer of the skin via the topical application of 5,6-O-isopropylidene L-ascorbic acid. This invention further provides a stable, cosmetically acceptable vehicle in which the 5,6-O-isopropylidene L-ascorbic acid can be applied to the skin.

7 Claims, No Drawings

METHOD FOR DELIVERING ASCORBIC ACID AND ACETONE TO THE DERMAL LAYER OF THE SKIN

BACKGROUND OF INVENTION

The present invention relates generally to the field of cosmetic compositions containing ascorbic acid and acetone in bioavailable form. In particular, this invention relates to a topically-applied composition incorporating a vitamin C derivative that is absorbed efficiently and that effectively establishes and maintains beneficial levels of ascorbic acid and acetone in the dermal layer of the skin.

Ascorbic acid, synonymously referred to herein as vitamin C, is essential in the human diet for the prevention of scurvy, a disease characterized by weakened connective tissue resulting from improper collagen production. The formation and maintenance of collagen, the fibrous constituent of bone, cartilage, and connective tissue, is a major function of vitamin C (Kivirikko, K. I., and R. Myllyla 1985 Ann. N.Y. Acad. Sci. 460: 187–201; Tajima, S., and S. R. Pinnell 1996. J. Dermatol. Sci. 11: 250–253). Human skin is particularly sensitive to the availability and action of ascorbic acid, as it is the largest organ in the body, and because the dermal layer of the skin is composed of approximately 70 to 80% collagen by dry weight. By stimulating and regulating the synthesis of collagen, vitamin C increases the elasticity and structural integrity of human skin and inhibits the formation of wrinkles. U.S. Pat. No. 4,983,382 suggests that supplementing dermal tissue with ascorbic acid delivered percutaneously through the stratum corneum can result in improved tone and luster, decrease in fine lines and wrinkles, and improved elasticity.

Another important benefit of ascorbic acid is its protective effect against oxidative damage to the skin. A major cause of cutaneous damage is the generation of reactive oxygen species by chemical pollutants, smoking, and particularly ultraviolet (UV) radiation. Reactive oxygen species can damage lipids, proteins, and nucleic acids in skin cells, which in turn can lead to the development of cutaneous cancer and photoaging (Fisher, G. J., Z. Q. Wang, S. C. Datta, J. Varani, S. Kang, and J. J. Voorhees 1997. N. Engl. J. Med. 337: 1419–1429). Ascorbic acid is a critical component of the nonenzymatic antioxidant defense system in the skin. At higher concentrations, ascorbic acid is known to neutralize singlet oxygen, superoxide anions, and hydroxy radicals in the skin before they can cause damage (Buettner, G. R., and B. A. Jurkiewicz. 1996. In: Cadenas, E., Packer, L., eds. Handbook of antioxidants. pp. 91–115).

Numerous investigators have reported that high levels of ascorbic acid in the skin, produced by topical application of the vitamin, provides some degree of protection against UV radiation, particularly UVA (Darr, D., S Dunston, H. Faust, and S. Pinnell. 1996. Acta Derm. Venereol. (Stockh). 76: 264–268; Black, H. S., and J. T. Chan. 1975. J. Invest. Dermatol. 65: 412–414). This protective effect is apparently due to the scavenging of oxygen free radicals generated in the cytosol by UVA rays. The concentration of ascorbic acid in the skin cell is inversely related to the level of oxygen free radical activity and thus the degree of cellular damage (Darr, D., S. Combs, S. Dunston, T. Manning, and S. Pinnell. 1992. Brit. J. Dermatol. 127: 247–253). Ascorbic acid also has a protective effect against cutaneous damage caused by UVB irradiation. When vitamin C was applied topically to pig and human skin prior to UVB irradiation, erythema and sunburn were prevented (Darr, D., S. Combs, S. Dunston, T. Manning, and S. Pinnell 1992. Brit. J. Dermatol. 127: 247–253; Murray, J., D. Darr, J. Reich, and S. Pinnell 1991. J. Invest. Dermatol. 96: 587). Photoaging changes in the skin of humans and of hairless mice were decreased after topical application of ascorbic acid (Traikovich, S. S. 1999. Arch. Otolaryngol. Head Neck Surg. 125: 1091–1098; Bissett, D. L., R. Chatterjee, and D. P. Hannon. 1990. Photoimmunol. Photomed. 7: 56–62).

Topical application of ascorbic acid has been shown to inhibit the release of histamine from cellular membranes, thus preventing allergic reactions among individuals with sensitive skin. Topical ascorbic acid was demonstrated to protect against UV-induced immunosuppression and tolerance to contact antigen in mice (Nakamura, T., S. R. Pinnell, D. Darr, et al. 1997. J. Invest. Dermatol. 109: 20–24). Finally, there is evidence that vitamin C can minimize age-related skin discoloration by inhibiting tyrosinase and the formation of melanin (Tomita, Y., A. Hariu, C. Mizumo, and M. Seyi. 1980. J. Invest. Dermatol. 75(5): 379–382; Maeda, K., and F. M. Arbutin 1996. J. Pharmacol. Exp. Ther. 276: 765–769).

All of the aforementioned beneficial effects of ascorbic acid, particularly those resulting from the antioxidant activity of this substance, will be optimized only if high levels of vitamin C are established and maintained in the tissues Uacques, P. F., and L. T. Chylack. 1991. Am. J. Clin. Nutr. 53: 352S–355S). Attempts to increase skin levels of ascorbic acid through increased ingestion have been futile because vitamin C concentration of the skin is regulated, and limited, by active transport mechanisms (Rumsey, S. C., and M. Levine. 1998. J. Nutr. Biochem. 9: 116–130). Alternatively, the direct delivery of a high concentration of ascorbic acid through the stratum corneum barrier into the skin will effectively increase the pool of protective antioxidants and enhance collagen synthesis. However, there are many obstacles that must be overcome to reach this goal. For example, as a water-soluble molecule, vitamin C is not stored well in the tissues and is rapidly removed from the body, with a half-life of about 20 days in the human (Ritchey, S. J. 1965. Am. J. Clin. Nutr. 17: 57–114). Also, because of its hydrophilic nature, vitamin C is not absorbed well into specific tissues, especially the skin, which naturally repels water and water-soluble substances. Depending on the vehicle used, only about 8% of topically-applied ascorbic acid is actually absorbed into the skin (Darr, D., S. Combs, S. Dunston, T. Manning, and S. Pinnell. 1991. J. Invest. Dermatol. 96: 590). In addition, ascorbic acid is very unstable in aqueous solutions at neutral pH (Meucci et al. 1985. Acta. Vitaminol. Enzymol. 7(3–4): 147–154). Taken together, the lack of stability and poor cutaneous absorption of ascorbic acid limit the effectiveness of most topical vitamin C preparations.

Numerous attempts have been made to overcome the aforementioned difficulties in order to deliver effective concentrations of ascorbic acid directly to the dermal layer of the skin. For example, the hydroxyl groups at carbon 2 and at carbon 3 have been esterified to phosphate groups to form ascorbyl-2-phosphate and ascorbyl-3-phosphate, respectively. These ascorbate derivatives are remarkably stable in aqueous solutions, but because of the negative charge of the phosphate groups, they do not traverse the stratum corneum. Topical application of a serum that contained 13 wt % of magnesium ascorbyl 2-phosphate failed to increase skin levels of ascorbic acid (Pinnell, S. R., H. Yang, M. Omar, et al. 2001. Dermatologic Surgery 27 (2): 137–142), verifying previous studies that had documented the marginal percutaneous absorption of this ascorbate derivative (Kobayashi, S., M. Takehana, S. Itoh, and E. Ogata. 1996. Photochemistry and Photobiology 64(1): 224–228).

In order to increase percutaneous absorption, ascorbate derivatives possessing a lipophilic moiety have been synthesized. U.S. Pat. No. 5,409,693 discloses topical application of lipophilic fatty acid esters of ascorbic acid to facilitate percutaneous absorption in the treatment of sunburn. Ascorbyl-6-palmitate, in which palmitic acid is esterified to the hydroxyl group at carbon 6 of ascorbic acid, is the fatty acid ester that is most widely used in topical vitamin C preparations. However, previous studies of ascorbyl-6-palmitate failed to demonstrate protection against photoaging in mouse skin (Bissett, D. L., R. Chatterjee, and D. P. Hannon. 1990. Photodermatol Photoimmunol Photomed 7: 56–62), and a recent study demonstrated that topical application of a serum containing 10 wt % of ascorby-6-palmitate resulted in no significant increase in skin levels of ascorbic acid (Pinnell, S. R., H. Yang, M. Omar, et al. 2001. Dermatologic Surgery. 27(2): 137–142).

Topical application of ascorbic acid in its unmodified form has been the most effective means of delivering vitamin C to the dermal layer of the skin (see U.S. Pat. No. 4,983,382; 5,140,043; 6,299,889). However, the results of recent studies indicate that ascorbic acid must be formulated at pH levels of less than 3.5 to enter the skin, and that the maximal concentration for optimal percutaneous absorption is 20 wt % (Pinnell, S. R., H. Yang, M. Omar, et al. 2001. Dermatologic Surgery. 27(2): 137–142). At this concentration and pH, ascorbic acid is known to disrupt the epidermis and irritate the skin such that most beneficial effects may be negated. In consideration of consumer acceptance, most commercial ascorbic acid formulations contain much less than 20 wt % of the vitamin and are maintained at a more neutral pH. Under these conditions, the absorption and effectiveness of ascorbic acid are limited.

Acetone in low concentrations is known to have beneficial effects in the skin. Acetone has been shown to have anti-inflammatory effects in cases of contact dermatitis (Sjogren, F., O. Groth, and C. Anderson. 1999. Contact Dermatitis. 41(1): 22–29). In inflamed skin treated with acetone, erythema and edema were diminished and there was observed a significant decrease in the presence of mononuclear cells, an indicator of inflammation. The reason for this is unclear, but it may be due to an alteration of intercellular lipid organization and cellular membrane lipid organization, thus influencing membrane receptor function. Despite its benefits, acetone applied directly to the skin in high concentrations can disrupt the structural integrity of the epidermis and cause dryness, resulting in skin irritation.

SUMMARY OF INVENTION

The object of the present invention is to provide a method of establishing and maintaining levels of ascorbic acid and acetone in the dermal layer of the skin sufficient to produce beneficial effects.

Ascorbic acid prevents oxidative damage and promotes collagen synthesis in the skin, and acetone has anti-inflammatory effects in the skin. However, topically-applied ascorbic acid is not well-absorbed, and direct application of acetone can disrupt the structural integrity of the skin.

The present invention overcomes the aforementioned problems by providing a composition for topical application that incorporates 5,6-O-isopropylidene L-ascorbic acid, a derivative of ascorbic acid that is more lipid soluble that ascorbic acid and thus better absorbed into the dermis with minimal disruption of the structural integrity of the skin. In the dermal layer of the skin, non-specific esterases hydrolyze 5,6-O-isopropylidene L-ascorbic acid to form ascorbic acid and acetone.

Another object of the present invention is to provide a stable, cosmetically-acceptable carrier in which 5,6-O-isopropylidene L-ascorbic acid can be applied topically.

DETAILED DESCRIPTION

The present invention provides a simple, efficient, and gentle method of increasing the concentration of ascorbic acid in the dermal layer of the skin, which comprises topical application of 5,6-O-isopropylidene-L-ascorbic acid in an amount that will effectively increase ascorbic acid concentration in the dermis.

The present invention also provides a method for enhancing the synthesis of skin collagen, which comprises increasing the ascorbic acid concentration of the dermal layer of the skin via the topical application of 5,6-O-isopropylidene L-ascorbic acid in an amount that will effectively increase ascorbic acid concentration in the dermis.

The present invention further provides a method for increasing the antioxidant potential of the skin, which comprises increasing the ascorbic acid concentration of the dermal layer of the skin via the topical application of 5,6-O-isopropylidene L-ascorbic acid in an amount that will effectively increase ascorbic acid concentration in the dermis.

The present invention provides a method of increasing the concentration of acetone in the dermal layer of the skin, which comprises topical application of 5,6-O-isopropylidene L-ascorbic acid in an amount that will effectively increase the acetone concentration in the dermis.

The present invention also provides a method for decreasing inflammation of the skin, which comprises increasing the acetone concentration of the dermal layer of the skin via the topical application of 5,6-O-isopropylidene L-ascorbic acid in an amount that will effectively increase acetone in the dermis.

As described in "Background of the Invention", increasing the concentration of ascorbic acid in the dermis is desired because this molecule provides numerous benefits which result in enhanced health and appearance of the skin. However, unmodified ascorbic acid is not absorbed well into the skin for several reasons.

Ascorbic acid is a water-soluble molecule. The hydrophilicity of ascorbic acid is attributed to hydroxyl groups at carbons 2, 3, 5, and 6 of the molecule. At a neutral pH, such as in water, these hydroxyl groups, particularly the groups at carbons 2 and 3, are unprotonated and thus carry a negative charge. The negative charges allow ascorbic acid to dissolve quickly and completely in an aqueous solution, but greatly limit the solubility of the molecule in a non-aqueous, organic environment such as the skin. Ascorbic acid at neutral pH also does not dissolve well in organic solvents commonly used in formulations for topical use, such as glycerin, propylene glycol, and various fats, thus limiting the usefulness of organic solvents as a vehicle for carrying ascorbic acid into the skin.

Absorption of ascorbic acid into an organic, non-aqueous material such as the skin requires that all hydroxyl groups be fully protonated, and this state occurs only at a pH of less than 4.2, the pKa of the molecule. The lower the pH, the more likely the hydroxyl groups of ascorbic acid will be protonated, thus making the molecule more lipophilic, or fat soluble. In addition, full protonation of the hydroxyl groups of ascorbic acid at low pH results in greater stability of the molecule.

Past attempts to increase the stability of ascorbic acid or to enhance the absorption of ascorbic acid into the skin have not been successful (see Background of the Invention). The most successful strategy to date has been to apply unmodified ascorbic acid directly to the skin. However, optimal absorption of unmodified ascorbic acid into the skin requires a relatively high concentration (20 wt %) and a low pH (pH 2.0). Even under these conditions, "optimal absorption" is only about 8% of the ascorbic acid applied to the skin. Also, a 20 wt % concentration of ascorbic acid at pH 2.0 is highly irritating to the skin, so consumer acceptance is limited.

The present invention provides an improved method for increasing vitamin C activity in the dermal layer of the skin via the topical application of ascorbic acid that has been chemically modified to enhance absorption, reduce acidity, and increase stability. In the present invention, said ascorbic acid derivative is 5,6-O-isopropylidene L-ascorbic acid. The chemical structure of 5,6-O-isopropylidene L-ascorbic acid (henceforth referred to as IAA) provides many advantages over the use of unmodified ascorbic acid (henceforth referred to as UAA).

In the UAA molecule, the hydroxyl groups at carbons 5 and 6 tend to withdraw electrons, thereby exerting a weak but significant inductive effect throughout the molecule. This electron-withdrawing inductive effect, acting through the molecular chain, increases the tendency of the hydrogens of hydroxyl groups at carbons 2 and/or 3 to dissociate as protons, leaving a negative charge. Polar repulsive forces resulting from the negative charges at the hydroxyl groups at carbons 2 and/or 3 can decrease stability of the molecule by inducing stereochemical strain, which in turn favors ring disruption. The negative charges also greatly decrease the solubility of UAA in non-aqueous, organic solvents and materials, such as the skin. The greater tendency of the hydroxyl hydrogens to dissociate as protons lowers the pKa and increases the acid strength of the molecule.

In the IAA molecule incorporated into the present invention, the three-carbon substituent bonded to the oxygen atoms at carbons 5 and 6 provide several advantages over the use of UAA:

1. The three-carbon substituent of IAA is much less electronegative than the hydroxyl groups of UAA and therefore does not withdraw electrons. The lack of an electron-withdrawing inductive effect results in an increase in pKa (4.8 for IAA vs. 4.2 for UAA), a decrease in the tendency of the hydroxyl hydrogens at carbons 2 and/or 3 to dissociate as protons, and thus a decrease in the acid strength of the molecule. The IAA molecule can therefore be applied topically at a more neutral pH which is less irritating to the skin.

2. The lack of an electron-withdrawing inductive effect and the subsequent tendency to remain fully protonated at a higher pH provides the IAA molecule with greater stability and thus a longer shelf life.

3. The IAA molecule is much more lipophilic than UAA because of the lipophilic, three-carbon substituent at carbons 5 and 6, and because of the greater tendency of the hydroxyl groups at carbons 2 and 3 to remain protonated. The lipophilic nature and relatively small size of IAA allows it to traverse the stratum corneum and to be absorbed efficiently into the dermal layer of the skin. In the dermis, nonspecific esterases hydrolyze the ester bonds between the three-carbon substituent and the oxygen atoms at carbons 5 and 6. The hydrolysis products are ascorbic acid and acetone.

A fortuitous finding of the present invention was that acetone, previously considered an inactive byproduct of the hydrolysis that liberates ascorbic acid, has anti-inflammatory effect in the skin (see "Background of the Invention"). Although a low concentration of acetone applied directly to the skin can provide an anti-inflammatory effect, this method tends to dehydrate the skin and to disrupt some of the lipid components of the skin. In the present invention, the introduction of small amounts of acetone into the skin via the absorption and hydrolysis of IAA produces the beneficial effects while preserving the structural integrity of the skin.

In accordance with the present invention, 5,6-O-isopropylidene L-ascorbic acid is solubilized in a dermatologically acceptable carrier and applied in effective amounts the skin. The invention will be described further in the following examples with are not to be construed as limiting the invention.

EXAMPLE 1

5,6-O-isopropylidene-L-ascorbic acid was synthesized by the addition of acetyl chloride (124.9 mL) to a slurry of L-ascorbic acid USP (1000 g) in acetone (4.5 L). The mixture was stirred vigorously at 35–30° C. After two hours, the crystalline product separated. The crystals were collected by filtration, washed with cold acetone, and dried in a vacuum desciccator over potassium hydroxide pellets. The product, produced in 77% yield, consisted of needle-shaped crystals with a melting point of 217–223° C.

EXAMPLE 2

For topical use, a homogeneous solution in accordance with the present invention containing 5.0 wt % 5,6-O-isopropylidene L-ascorbic acid was prepared by mixing the ingredients shown in TABLE 1. The ingredients were added in the order given and in the given amounts. The solution was prepared in a glass container with continuous stirring. After the addition of the zinc sulfate, and again after the addition of the glycerin, the solution was heated to approximately 60° C. The heating increased the solubility of the 2-phenoxyethanol and of the 5,6-O-isopropylidene L-ascorbic acid. The solution was then filtered through a fine plastic mesh, yielding a clear, colorless to very pale yellow liquid. The 5,6-O-isopropylidene L-ascorbic acid in this solution will retain its potency for approximately six months if the solution is stored at room temperature in a bottle that is impervious to ultraviolet light. In darkness at 10° C., 5,6-O-isopropylidene L-ascorbic acid in solution will remain stable and potent for approximately 18 months.

TABLE 1

5,6-O-isopropylidene L-ascorbic acid composition (Amounts in Weight %)

| Ingredient | Amount |
| --- | --- |
| Demineralized, deionized water | 57.5 |
| Zinc Sulfate | 0.125 |
| 2-Phenoxyethanol | 2.5 |
| Propylene Glycol | 20.0 |
| Glycerin | 20.0 |
| 5,6-O-isopropylidene L-ascorbic acid | 5.0 |

The present invention may be embodied in other specific forms without departing from the spirit or essential attributes thereof. Therefore, it would be apparent to those skilled in the art to make variations and modifications thereof without departing from the scope of the appended claims.

What is claimed is:

1. A method of increasing the concentration of ascorbic acid and acetone in the skin which method comprises hydrolyzing a composition comprising 5,6-O- isopropylidene L-ascorbic acid, propylene glycol, glycerin, 2-phenoxyethanol, zinc sulfate and water by the action of nonspecific esterases located in the dermal layer of the skin upon topical application of said composition wherein the composition hydrolyzed is used in a therapeutically effective amount.

2. The method of claim 1, wherein the 5,6-O-isopropylidene L-ascorbic acid is used in solution and is present from 1.0 wt % to 15.0 wt % of the total weight of the solution.

3. The method of claim 1, wherein the propylene glycol is used in solution and is present from 10.0 wt % to 30.0 wt % of the total weight of the solution.

4. The method of claim 1, wherein the glycerin is used in solution and is present from 10.0 wt % to 30.0 wt % of the total weight of the solution.

5. The method of claim 1, wherein the 2-phenoxyethanol is used in solution and is present from 2.0 wt % to 3.0 wt % of the total weight of the solution.

6. The method of claim 1, wherein the zinc sulfate is used in solution and is present from 0.1 wt % to 0.2 wt % of the total weight of the solution.

7. The method of claim 1, wherein the water is present from about 50.0 wt % to 60.0 wt % of the total weight.

* * * * *